US010835443B2

(12) United States Patent
Tsai et al.

(10) Patent No.: US 10,835,443 B2
(45) Date of Patent: Nov. 17, 2020

(54) EXOSKELETON ROBOT

(71) Applicant: FREE BIONICS TAIWAN INC., Hsinchu (TW)

(72) Inventors: Yi-Jeng Tsai, Taoyuan (TW); Ming-Chang Teng, Hsinchu (TW)

(73) Assignee: FREE BIONICS TAIWAN INC., Hsinchu (TW)

(*) Notice: Subject to any disclaimer, the term of this patent is extended or adjusted under 35 U.S.C. 154(b) by 221 days.

(21) Appl. No.: 15/811,102

(22) Filed: Nov. 13, 2017

(65) Prior Publication Data
US 2018/0200878 A1 Jul. 19, 2018

Related U.S. Application Data

(60) Provisional application No. 62/445,940, filed on Jan. 13, 2017.

(51) Int. Cl.
*A61H 3/00* (2006.01)
*A61H 1/02* (2006.01)
(Continued)

(52) U.S. Cl.
CPC ............... *A61H 3/00* (2013.01); *A61F 2/70* (2013.01); *A61H 1/0262* (2013.01);
(Continued)

(58) Field of Classification Search
CPC .... A61H 2201/1207; A61H 2201/1676; A61H 2201/1671; A61H 2201/0192;
(Continued)

(56) References Cited

U.S. PATENT DOCUMENTS 3,827,430 A    8/1974  Fadden
6,983,988 B1 * 1/2006  Lo ............................ B62J 1/28
                                            297/215.1
(Continued)

FOREIGN PATENT DOCUMENTS

CN    104042428    9/2014
CN    204951524    1/2016
(Continued)

OTHER PUBLICATIONS

TIPO office action dated May 10, 2018 for related Taiwan application TW 107109633.
(Continued)

*Primary Examiner* — Michael J Tsai
(74) *Attorney, Agent, or Firm* — WPAT, P.C., Intellectual Property Attorneys; Anthony King

(57) ABSTRACT

An exoskeleton robot comprises a waist assembly and a leg assembly. The waist assembly includes a first frame, a plate and a second frame. The first frame includes a rail and a slider inside the rail. The plate is fixed by a first bolt screwed into the slider. The second frame is connected to the plate. The second frame having a slot and a second bolt inside the slot. The leg assembly is installed to the second frame by the second bolt. By loosening the bolts, a user can move the leg assembly in two directions of the rail and the slot without the requirement for detaching the bolts.

20 Claims, 18 Drawing Sheets

(51) Int. Cl.
*A61F 2/70* (2006.01)
*B25J 9/00* (2006.01)

(52) U.S. Cl.
CPC .......... *A61H 1/0266* (2013.01); *B25J 9/0006* (2013.01); *A61H 2201/0192* (2013.01); *A61H 2201/1207* (2013.01); *A61H 2201/164* (2013.01); *A61H 2201/165* (2013.01); *A61H 2201/1671* (2013.01); *A61H 2201/1676* (2013.01); *A61H 2205/12* (2013.01)

(58) Field of Classification Search
CPC .......... A61H 2201/164; A61H 2205/12; A61H 1/02–0296; A61H 1/024; A61H 1/0244; A61H 1/0262; A61H 1/0266; A61H 1/0274; A61H 1/0277; A61H 1/0281; A61H 1/0292; A61H 2201/1619; A61H 2205/084; A61H 2201/165; A61H 2201/1642; A61H 2201/163; A61H 2003/007; A61H 2001/0211; A61H 3/00–3/008; A61H 1/0237–2001/027; A61F 2/70; A61F 5/00; A61F 5/0102; A61F 2005/0146; A61F 5/04–048; A61F 5/02–028; A61F 5/026; A61F 5/024; A61F 2/60–2002/807; A61F 5/01–2005/0188; A61F 4/00; B25J 9/0006; B25J 9/0003; B25J 9/162; B25J 5/00–5/06; A43C 11/16; B62D 57/032; Y10S 901/01; Y10S 601/05; Y10S 601/33–35; Y10S 602/23–31; Y10S 700/245–264; Y10S 700/90; Y10S 318/568; Y10S 318/12; Y10S 607/49; Y10S 623/24–56
USPC .......................................... 602/19, 23, 32, 36
See application file for complete search history.

(56) References Cited

U.S. PATENT DOCUMENTS

| | | | |
|---|---|---|---|
| 8,070,700 | B2 | 12/2011 | Kazerooni et al. |
| 9,687,409 | B2 | 6/2017 | Teng et al. |
| 2006/0052731 | A1* | 3/2006 | Shimada ................. A61H 3/00 602/5 |
| 2006/0064047 | A1* | 3/2006 | Shimada .............. A61H 1/0255 602/23 |
| 2010/0204627 | A1* | 8/2010 | Kazerooni .......... A61H 1/0266 602/16 |
| 2014/0100493 | A1 | 4/2014 | Craig et al. |
| 2014/0100501 | A1* | 4/2014 | Burke .................... A61F 5/028 602/19 |
| 2015/0272810 | A1* | 10/2015 | Teng .................... A61H 1/0244 601/34 |
| 2015/0335515 | A1* | 11/2015 | Lee .......................... A61H 3/00 601/5 |
| 2015/0351995 | A1 | 12/2015 | Zoss et al. |
| 2015/0366694 | A1* | 12/2015 | Bujold .................. A61F 5/0102 602/16 |
| 2016/0339583 | A1 | 11/2016 | Van Engelhoven et al. |
| 2018/0318122 | A1* | 11/2018 | LeCursi ............... A61B 5/1077 |

FOREIGN PATENT DOCUMENTS

| | | |
|---|---|---|
| CN | 106002950 | 10/2016 |
| CN | 105105896 | 11/2016 |
| CN | 104940003 A | 6/2017 |
| CN | 106821684 A | 6/2017 |
| EP | 2923685 | 9/2015 |
| JP | 1995-29891 A | 6/1995 |
| JP | 2010125030 A | 6/2010 |
| JP | 2011110176 A | 6/2011 |
| JP | 2013-173190 A | 9/2013 |
| JP | 2015188740 A | 11/2015 |
| JP | 2017-94427 A | 6/2017 |
| TW | 201436780 A | 10/2014 |
| TW | 201436780 | 11/2015 |
| TW | 201536267 | 11/2016 |
| WO | 2016146960 | 9/2016 |

OTHER PUBLICATIONS

English Abstract Translation of Office Action for related Taiwan application TW 107109633.
English Abstract Translation of TW 201536267A.
Abstract Translation of TW 201436780.
EPO search report dated Jan. 9, 2019 for related EP application 18178308.
Office Action from JPO dated Mar. 13, 2019 for related JP application 2018-077513.
EPO search report and provisional opinion dated Jan. 17, 2019 for related EP application 18178307.
Office Action from JPO dated Oct. 9, 2019 for related JP application 2018-077513.
Office Action from JPO dated Mar. 13, 2019 for related JP application 2018-077510.
Office Action from CNIPA dated Aug. 28, 2020 for related CN application 201810316408.8.
Search Report from CNIPA dated Aug. 28, 2020 for related CN application 201810316408.8.

* cited by examiner

EXOSKELETON ROBOT

CROSS REFERENCE TO RELATED APPLICATIONS

This application claims priority to U.S. provisional application Ser. No. 62/445,940, filed 13 Jan. 2017, which is incorporated herein by reference in its entirety.

TECHNICAL FIELD

The present disclosure relates generally to a walking assist device and, more particularly, to an exoskeleton robot.

DISCUSSION OF THE BACKGROUND

An exoskeleton robot, which is also known as powered armor, is a wearable mobile machine that supports the body of a user and moves limbs of the user. Generally, an exoskeleton is powered by a system of electric motors, pneumatics, levers, hydraulics, or a combination of technologies that can move limbs. One of the main applications is medical. The exoskeleton robot can help persons who lose or lose control of their legs or arms due to illness or accidental injury.

While the exoskeleton robots are worn by patients in hospitals or rehabilitation centers, the care workers need to adjust the exoskeleton robots to fit patients with a variety of body sizes. Moreover, patients with different injured parts also need different adjustments of the exoskeleton robots.

However, the structures of the traditional exoskeleton robots require the care workers to completely disassemble bolts or screws to adjust sizes of the traditional exoskeleton robots, and thus waste a lot of time and manpower.

Therefore, to save time and manpower, there is a requirement to quickly adjust the exoskeleton robots to fit patients with a variety of body sizes or different injured parts.

SUMMARY

An embodiment of the present disclosure provides an exoskeleton robot comprises a waist assembly and a leg assembly. The waist assembly includes a first frame, a plate and a second frame. The first frame includes a rail and a slider inside the rail. The plate is fixed by a first bolt screwed into the slider. The second frame is connected to the plate. The second frame having a slot and a second bolt inside the slot. The leg assembly is installed to the second frame by the second bolt.

Some embodiments of the present disclosure provide an exoskeleton robot with the slots and the rails to connect two elements, such as frames, assemblies or stands, of the exoskeleton robot, and a relative position of the two elements is adjustable by sliding the slider, the screws or the bolts without fully disengaging the screws or the bolts from the elements. Thus, there are advantages to save effort to adjust the relative position of the elements of the exoskeleton robot to fully meet adjustment requirements, including a waist width, a chest support height, a chest width, a hip depth, a thigh length, a thigh circumference, a shank length, and a shank circumference.

The foregoing has outlined rather broadly the features and technical advantages of the present disclosure in order that the detailed description of the disclosure that follows may be better understood. Additional features and advantages of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

A more complete understanding of the present disclosure may be derived by referring to the detailed description and claims when considered in connection with the Figures, where like reference numbers refer to similar elements throughout the Figures.

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
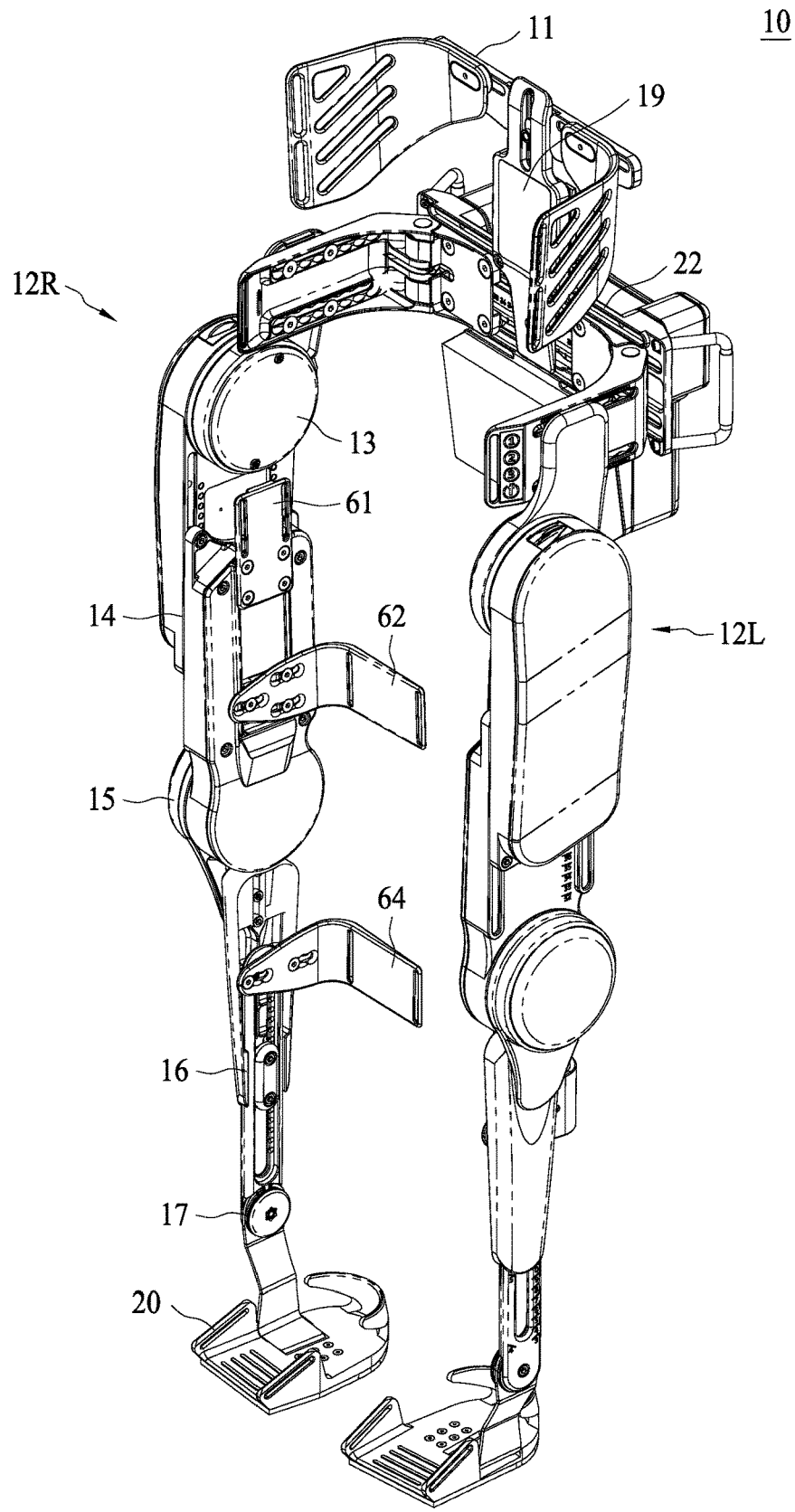
FIG. 1 is a perspective view of an exoskeleton robot based on an embodiment of the present disclosure.

Embodiments, or examples, of the disclosure illustrated in the drawings are now described using specific language. It shall be understood that no limitation of the scope of the disclosure is hereby intended. Any alteration or modification of the described embodiments, and any further applications of principles described in this document, are to be considered as normally occurring to one of ordinary skill in the art to which the disclosure relates. Reference numerals may be repeated throughout the embodiments, but this does not necessarily mean that feature(s) of one embodiment apply to another embodiment, even if they share the same reference numeral.

It shall be understood that, although the terms first, second, third, etc. may be used herein to describe various elements, components, regions, layers or sections, these elements, components, regions, layers or sections are not limited by these terms. Rather, these terms are merely used to distinguish one element, component, region, layer or section from another region, layer or section. Thus, a first element, component, region, layer or section discussed below could be termed a second element, component, region, layer or section without departing from the teachings of the present inventive concept.

The terminology used herein is for the purpose of describing particular example embodiments only and is not intended to be limited to the present inventive concept. As used herein, the singular forms "a," "an" and "the" are intended to include the plural forms as well, unless the context clearly indicates otherwise. It shall be further understood that the terms "comprises" and "comprising," when used in this specification, point out the presence of stated features, integers, steps, operations, elements, or components, but do not preclude the presence or addition of one or more other features, integers, steps, operations, elements, components, or groups thereof.

FIG. 1 is a perspective view of an exoskeleton robot 10 in accordance with some embodiments of the present disclosure. Referring to FIG. 1, the exoskeleton robot 10 includes a chest assembly 11, a back stand 19, a waist assembly 22, a right leg assembly 12R, and a left leg assembly 12L.

The chest assembly 11 is installed in the back stand 19, and the back stand 19 is installed in the waist assembly 22. Each of the right leg assembly 12R and the left leg assembly 12L is connected to the waist assembly 22 via a respective hip joint 13. Since the right leg assembly 12R and the left leg assembly 12L are symmetric in physical configuration to each other, for convenience, only the right leg assembly 12R is discussed.

The right leg assembly 12R includes a thigh stand 14, a shank stand 16, a knee joint 15, an ankle joint 17, and a shoe assembly 20 in addition to the hip joint 13.

The thigh stand 14, having an elongated shape, is pivotally connected at one end to the waist assembly 22 via the hip joint 13, and pivotally connected at another end to the shank stand 16 via the knee joint 15. As a result, the thigh stand 14 and the shank stand 16 are rotatable with respect to the knee joint 15.

The shank stand 16, also having an elongated shape, is pivotally connected at one end to the thigh stand 14 via the knee joint 15, and pivotally connected at another end to the shoe assembly 20 via the ankle joint 17. As a result, the shank stand 16 and the right shoe assembly 20 are rotatable with respect to the ankle joint 17.

Figure 2:
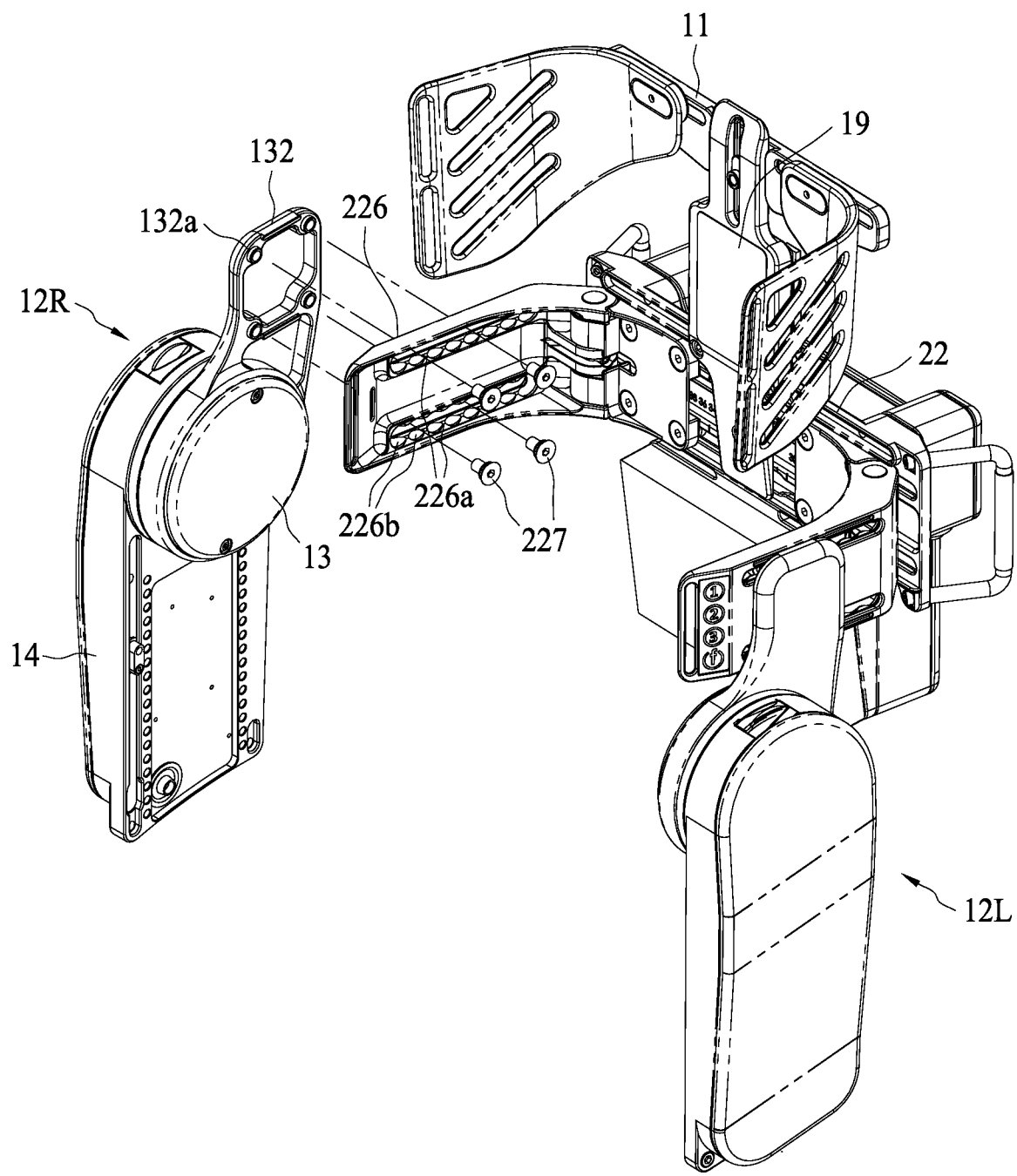
FIG. 2 is a perspective view illustrating a structure to assemble the right leg assembly to the waist assembly in accordance with some embodiments of the present disclosure.

FIG. 2 is a perspective view illustrating the structure to assemble the right leg assembly 12r to the waist assembly 22 in accordance with some embodiments of the present disclosure. Referring to FIG. 2, a second frame 226 includes two horizontal first slots 226a. A hip frame 132 of the right leg assembly 12r is installed in the second frame 226 of the waist assembly 22 by second bolts 227 passing through the two horizontal first slots 226a of the second frame 226 and screwed into holes 132a of the hip frame 132. Further, the first slots 226a include multiple indentations 226b along the first slots 226a to fit heads of the second bolts 227.

By loosening but not detaching the second bolts 227 from holes 132a of the hip frame 132, the user can slide the second bolts 227 in the two horizontal first slots 226a to adjust a relative horizontal distance between the right leg assembly 12R and the buttock pad 221 to fit the hip of the user.

Figure 3:
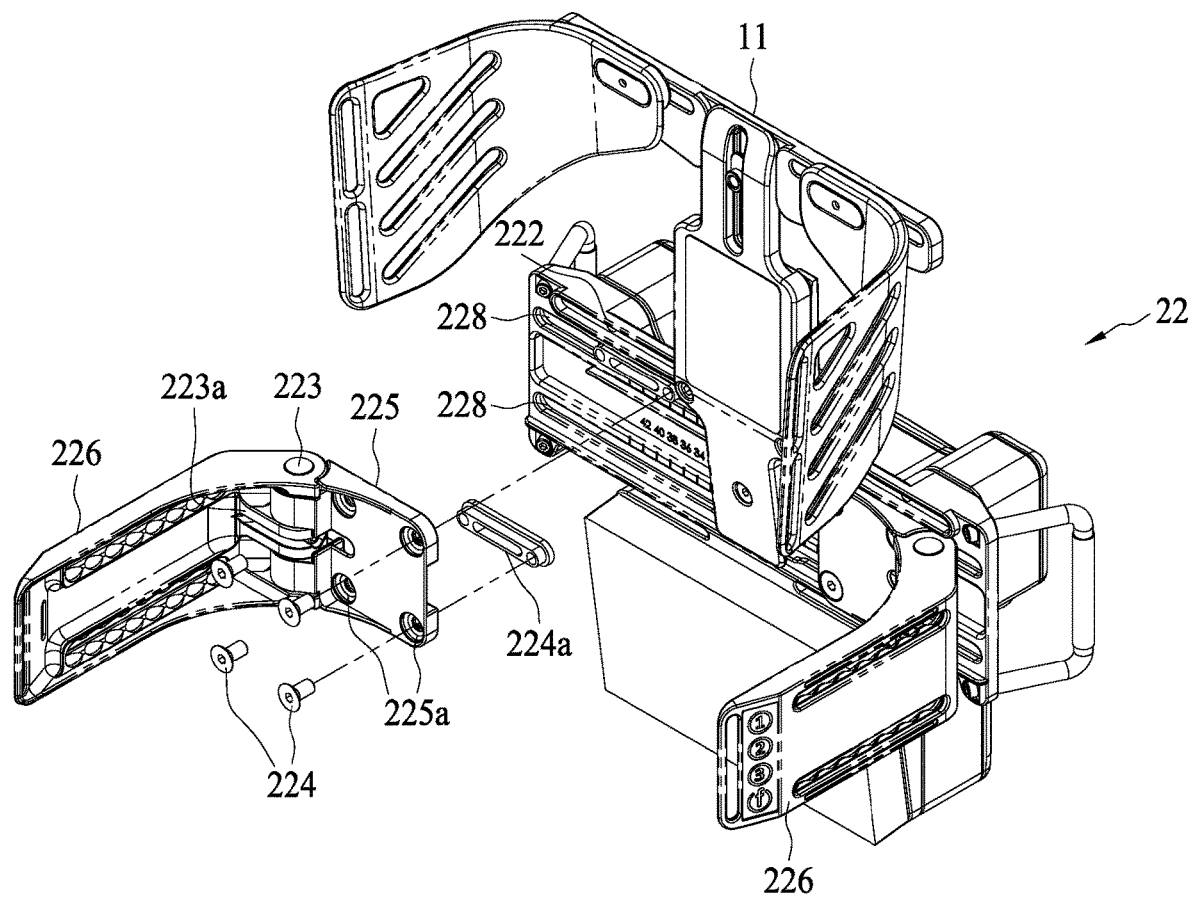
FIG. 3 is a perspective view illustrating a structure to assemble the waist assembly in accordance with some embodiments of the present disclosure.

FIG. 3 is a perspective view illustrating the structure to assemble the waist assembly 22 in accordance with some embodiments of the present disclosure. Referring to FIG. 3, the second frame 226 is installed in an install plate 225 by a waist joint 223, and thus the second frame 226 is pivotally connected to the install plate 225. Further, the install plate 225 is installed in a first frame 222 by first bolts 224 passing through holes 225a of the install plate 225 and screwed into first sliders 224a.

Figure 4:
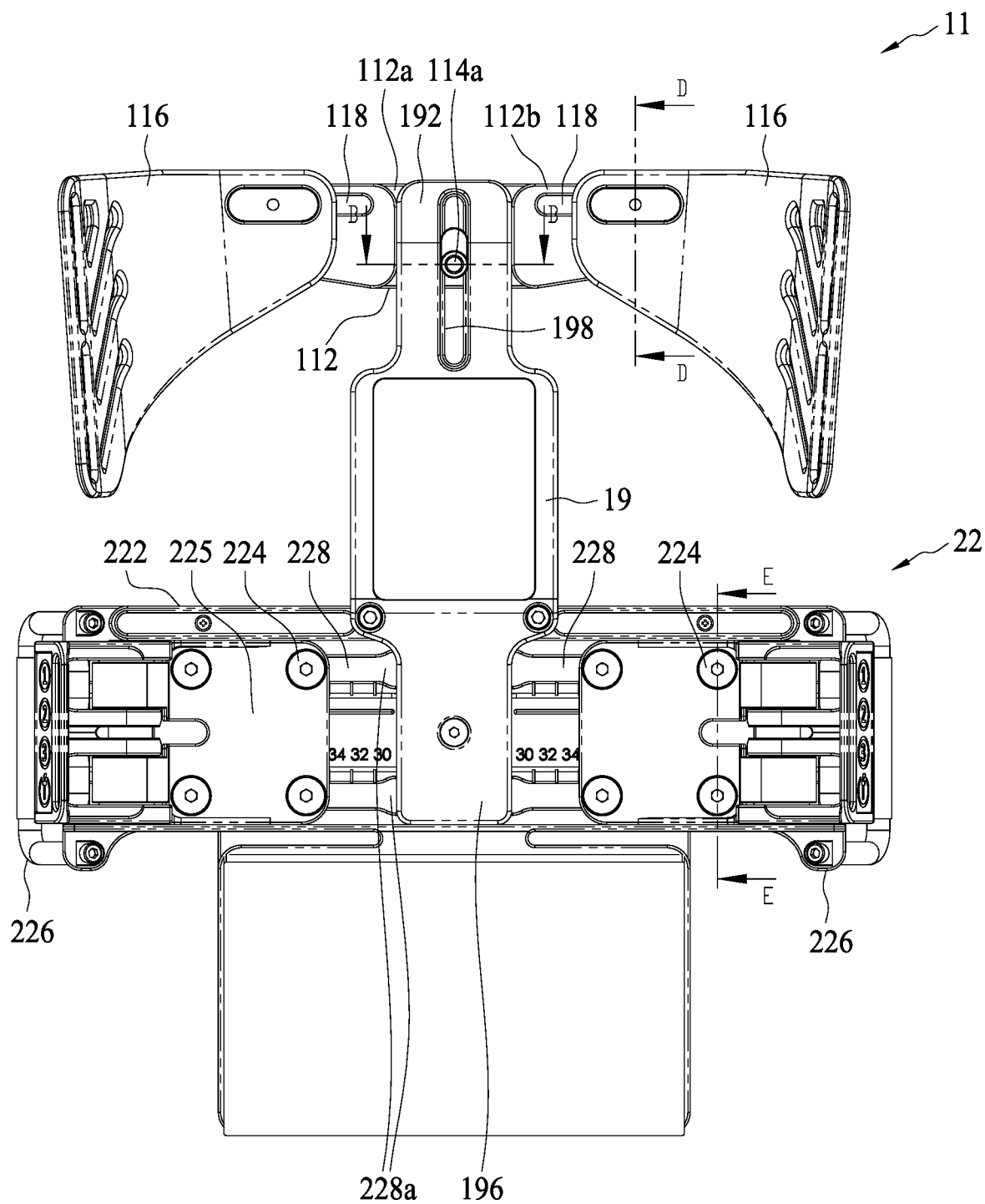
FIG. 4 is a front view of a structure of the chest assembly and the waist assembly in accordance with some embodiments of the present disclosure.

FIG. 4 is a front view of the structure of the chest assembly 11 and the waist assembly 22 in accordance with some embodiments of the present disclosure. Referring to FIGS. 3 and 4, the first frame 222 includes two first rails 228, and each of the first rails 228 includes two expanded sections 228a. The first sliders 224a are put into the first rails 228 of the first frame 222 through expanded sections 228a of the first rails 228, and then the expanded sections 228a can be covered by a rail cover 196 of the back stand 19. The first rails 228 are horizontal and allow the first sliders 224a to move horizontally.

The back stand 19 is installed in the waist assembly 22 by bolting the rail cover 196 in the first frame 222 of the waist assembly 22. The first sliders 224a can be moved along the first rails 228. Therefore, by loosening but not detaching the first bolts 224 from the first sliders 224a, the user can slide the first sliders 224a in the first rails 228 to adjust a relative horizontal distance between the second frames 226, and the waist assembly 22 can be configured to fit and support a user of the exoskeleton robot 10 at the waist and the hip.

Figure 5:
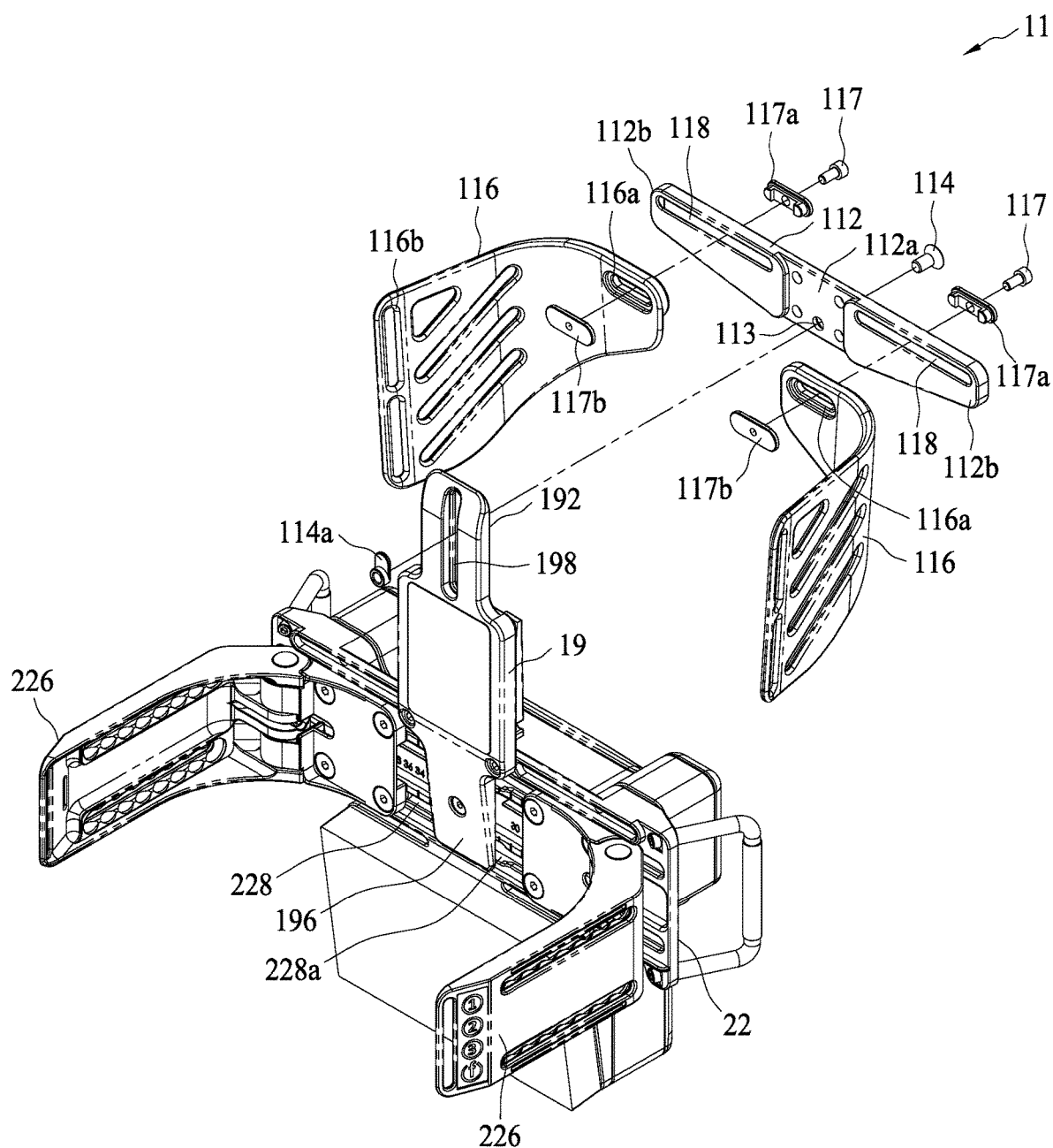
FIG. 5 is a perspective view illustrating a structure to assemble the chest assembly to the back stand and the waist assembly in accordance with some embodiments of the present disclosure.

FIG. 5 is a perspective view illustrating the structure to assemble the chest assembly 11 to the back stand 19 and the waist assembly 22 in accordance with some embodiments of the present disclosure. Referring to FIG. 5, the chest assembly 11 is installed in the back stand 19 by a bolt 114 passing through a hole 113 of the center part 112a of a third frame 112 of the chest assembly 11, and screwed into a third slider 114a in a third rail 198. The third slider 114a is inside the third rail 198 of the back frame 192 of the back stand 19 and can be moved along the third rail 198. Thus, by loosening but not detaching the bolt 114 from the third slider 114a, the user can slide the third slider 114a in the third rails 198 to adjust a vertical height of the chest assembly 11.

Further, the chest boards 116 are installed in wings 112b of the third frame 112 by third bolts 117 through second sliders 117a, second rails 118 of the wings 112b of the third frame 112, slots 116a of the chest boards 116, and slot covers 117b. Because the second sliders 117a engage with the slots 116a, and thus the position of the second sliders 117a in the second rails 118 can be slid to adjust a relative horizontal distance between side boards 116b of the chest boards 116 by loosening but not detaching the third bolts 117 from the second sliders 117a. Therefore, the chest assembly 11 can be configured to fit and support a user of the exoskeleton robot 10 at the chest.

Figure 6A:
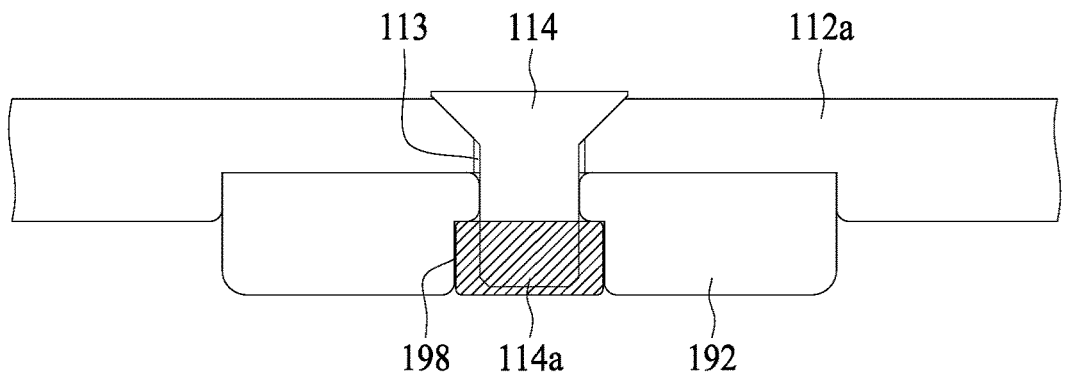
FIGS. 6A-6C are cross-sectional views along Lines B-B, D-D, and E-E of FIG. 4.

FIG. 6A is a cross-sectional view along Line B-B of FIG. 4. Referring to FIGS. 4 and 6A, the bolt 114 passes through the hole 113 of the center part 112a, the third rail 198, and the third slider 114a. The cross-section of the third rail 198 is a groove with two steps in two sides to contain the third slider 114a and prevent the third slider 114a from being pulled out of the third rail 198.

Figure 6B:
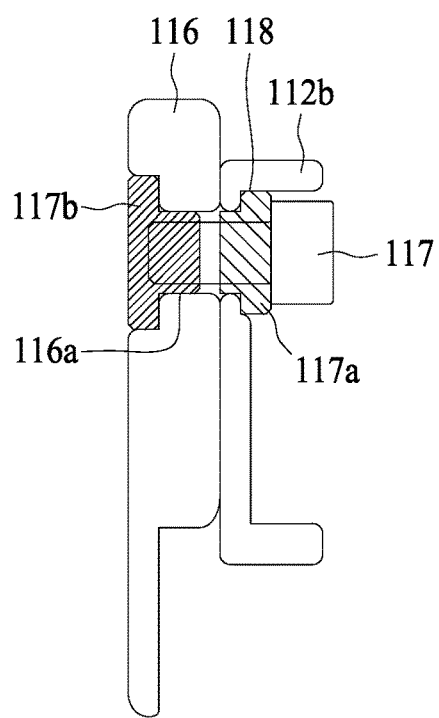

FIG. 6B is a cross-sectional view along Line D-D of FIG. 4. Referring to FIGS. 4 and 6B, the third bolt 117 passes through the second sliders 117a, second rails 118 of the wings 112b, the slots 116a of the chest boards 116, and the slot covers 117b. The cross-section of the second rail 118 is a groove with two steps in two sides to contain the second slider 117a and prevent the second slider 117a from being pulled out of the second rail 118.

Figure 6C:
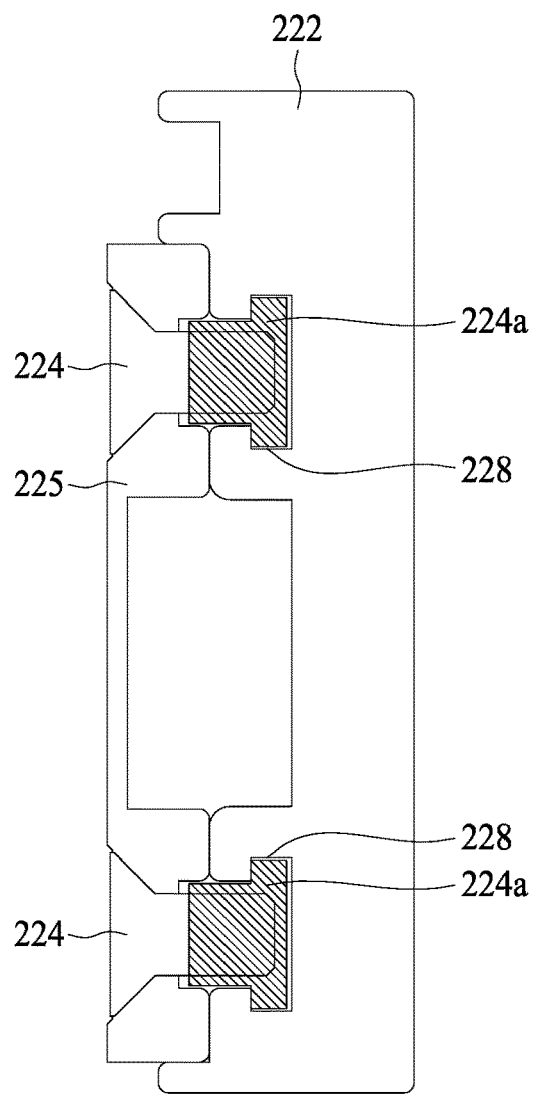

FIG. 6C is a cross-sectional view along Line E-E of FIG. 4. Referring to FIGS. 4 and 6C, first bolts 224 are screwed into the first sliders 224a, and the install plate 225. The first sliders 224a are inside the first rails 228. The cross-section of the first rail 228 is a groove with two steps in two sides to contain the first slider 224a and prevent the first slider 224a from being pulled out of the first rail 228.

Figure 7A:
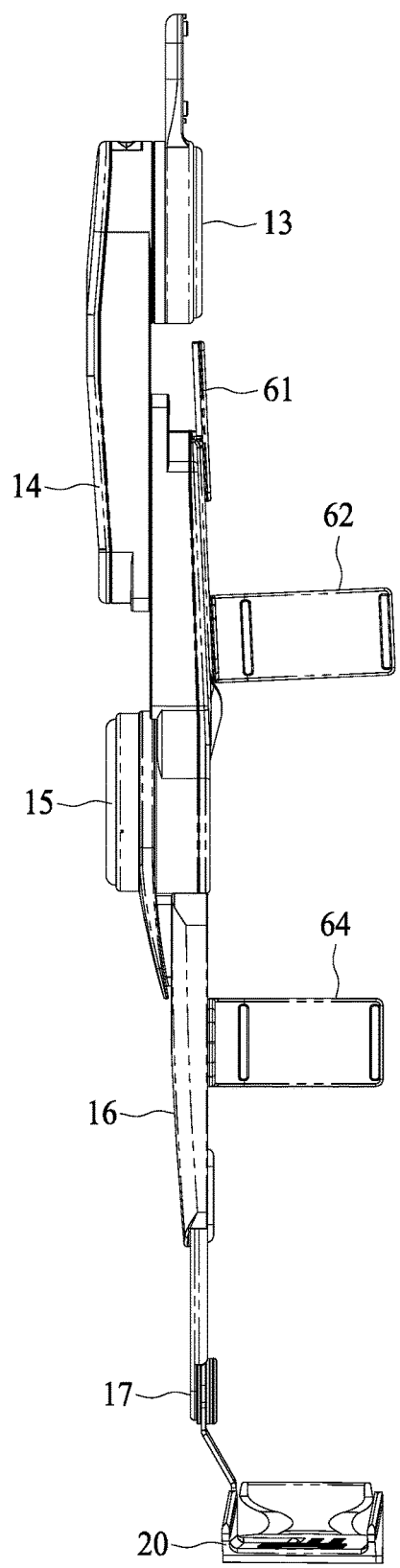
FIG. 7A is a front view of the right leg assembly in accordance with some embodiments of the present disclosure.
Figure 7B:
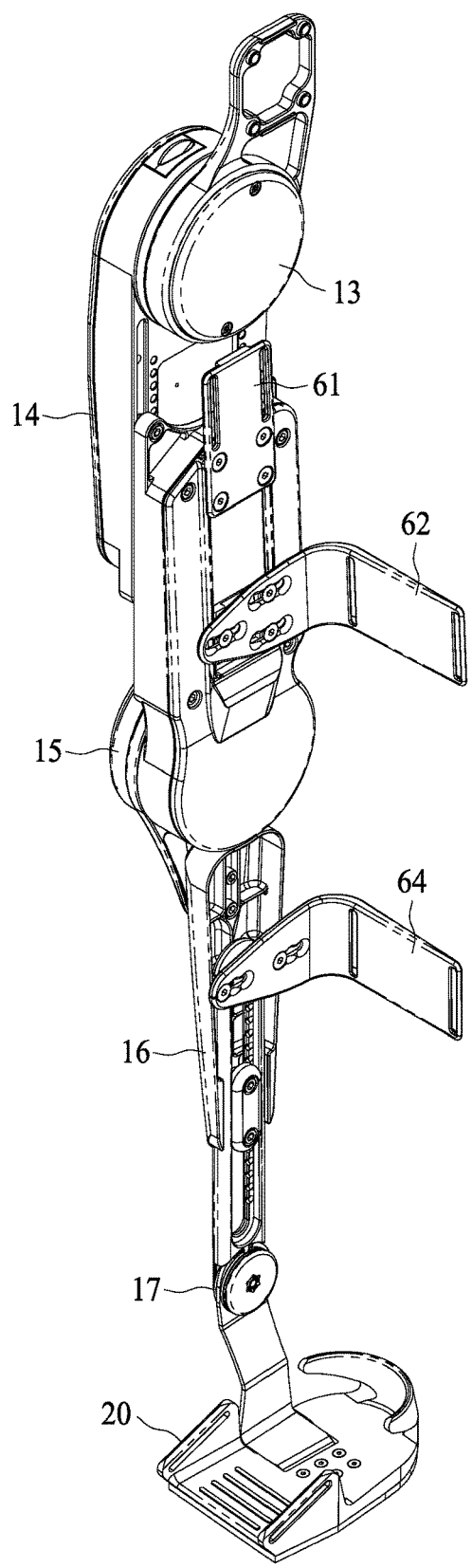
FIG. 7B is a perspective view of the right leg assembly in accordance with some embodiments of the present disclosure.

FIG. 7A is a front view of the right leg assembly 12R in accordance with some embodiments of the present disclosure. FIG. 7B is a perspective view of the right leg assembly 12R in accordance with some embodiments of the present disclosure.

Figure 8A:
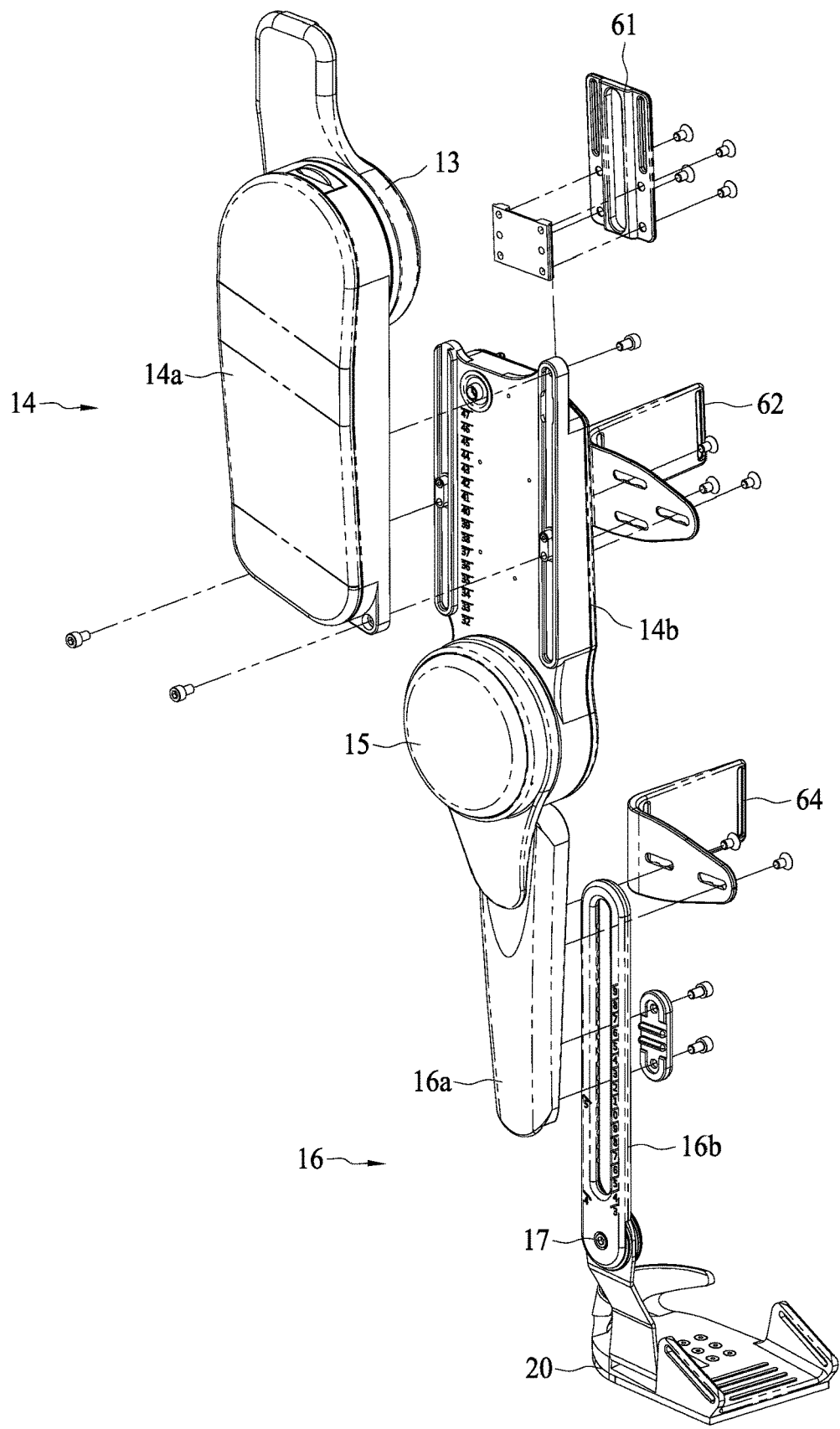
FIG. 8A is an exploded view of the right leg assembly viewed from the right side in accordance with some embodiments of the present disclosure.
Figure 8B:
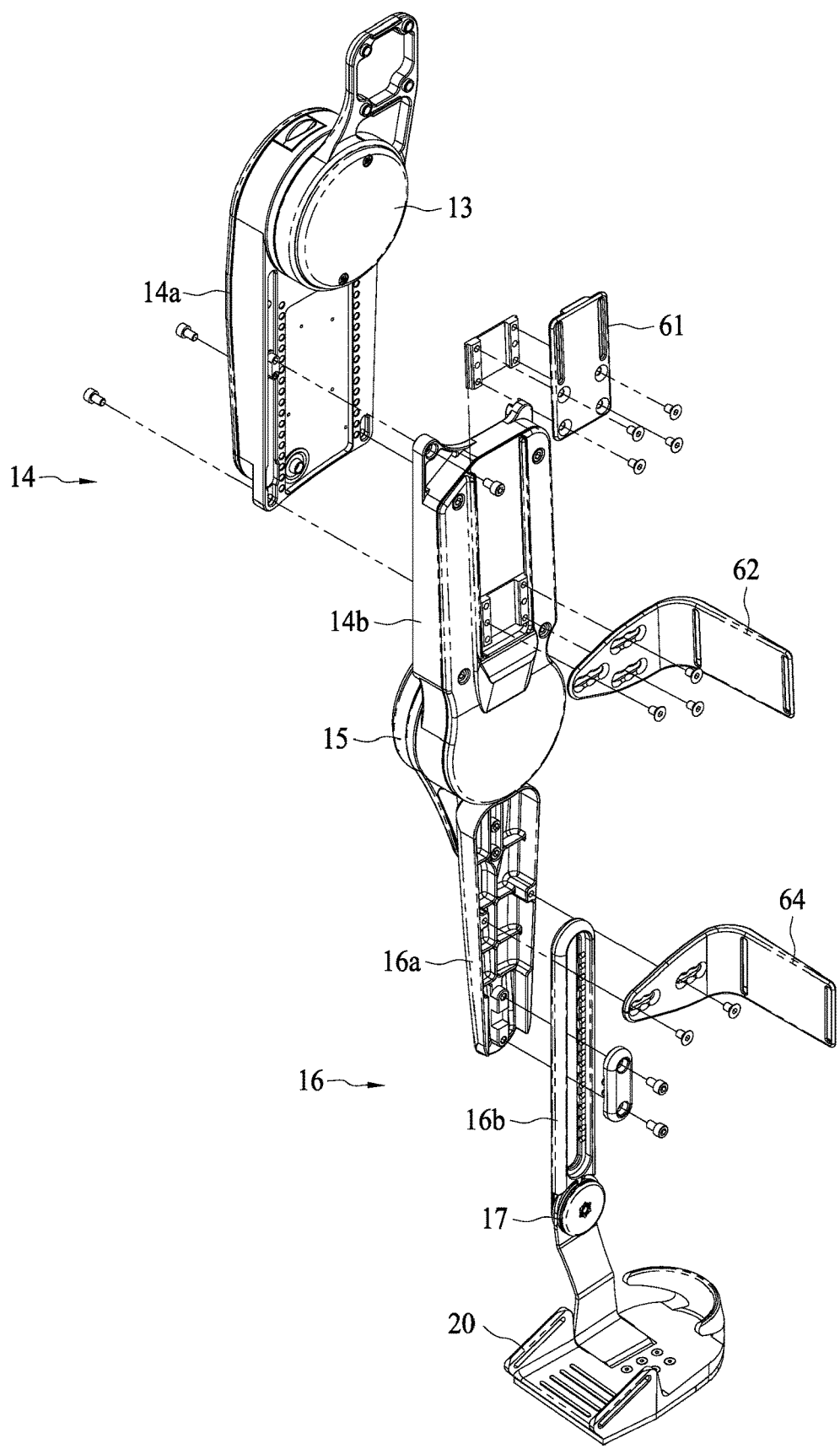
FIG. 8B is an exploded view of the right leg assembly viewed from the left side in accordance with some embodiments of the present disclosure.

FIG. 8A is an exploded view of the right leg assembly 12R viewed from the right side in accordance with some embodiments of the present disclosure. FIG. 8B is an exploded view of the right leg assembly 12R viewed from the left side in accordance with some embodiments of the present disclosure.

Figure 9A:
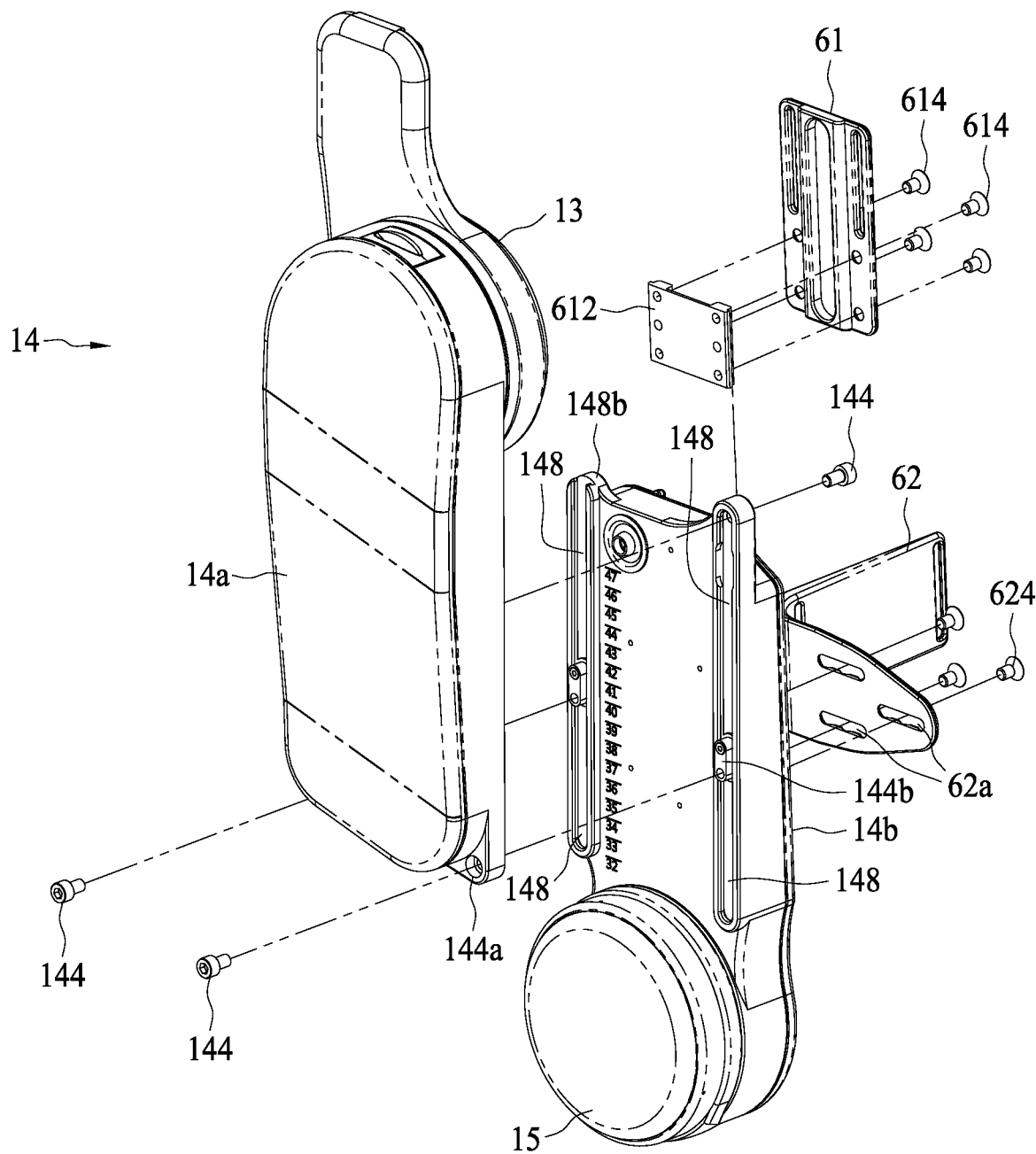
FIG. 9A is an exploded view of the thigh stand viewed from the right side in accordance with some embodiments of the present disclosure.
Figure 9B:
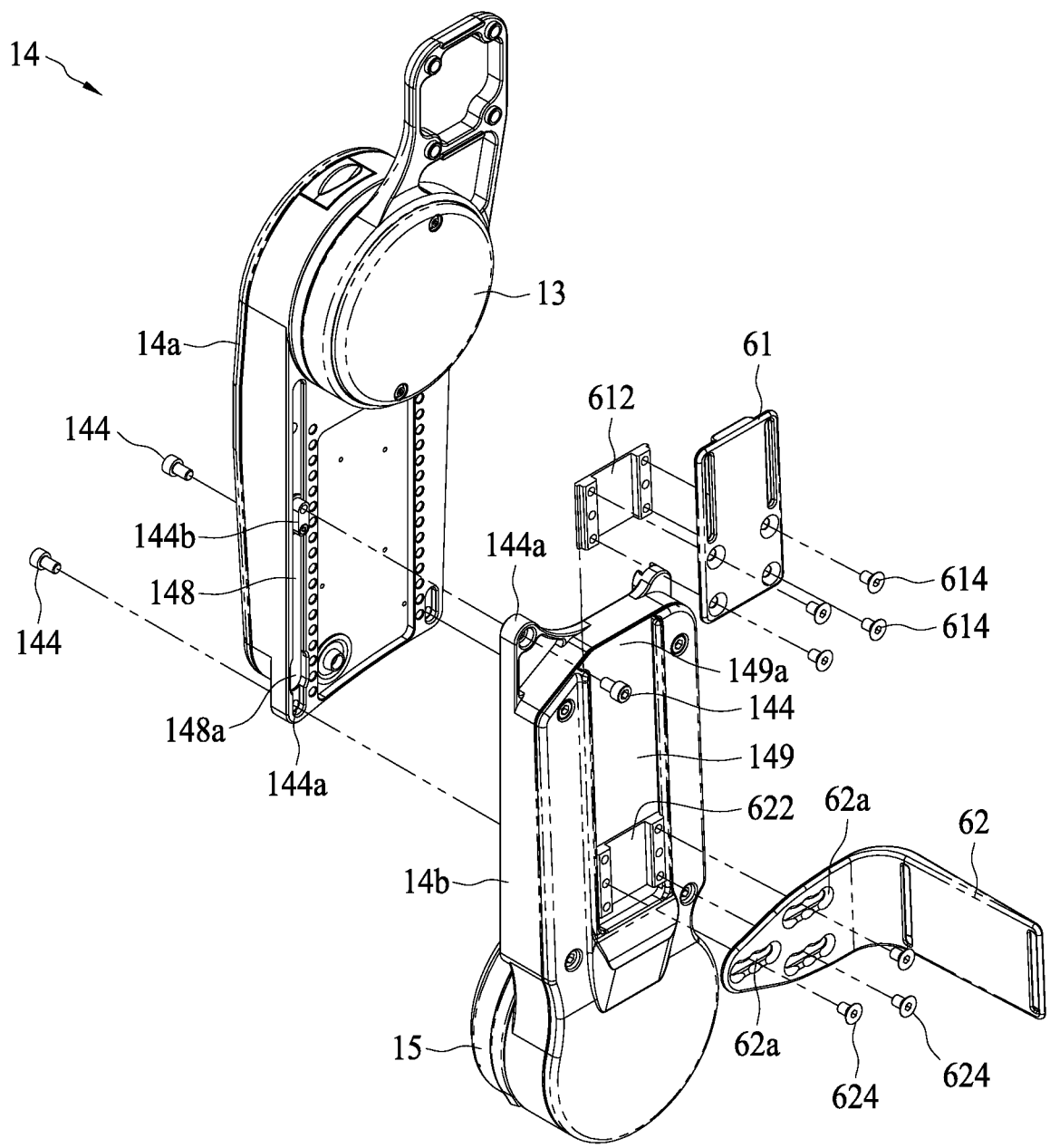
FIG. 9B is an exploded view of the thigh stand viewed from the left side in accordance with some embodiments of the present disclosure.

FIG. 9A is an exploded view of the thigh stand 14 viewed from the right side in accordance with some embodiments of the present disclosure. FIG. 9B is an exploded view of the thigh stand 14 viewed from the left side in accordance with some embodiments of the present disclosure. Referring to FIGS. 9A and 9B, the thigh stand 14 includes an upper thigh stand 14a and a lower thigh stand 14b.

The upper thigh stand 14a is pivotally connected to the hip joint 13, and has two holes 144a, a vertical fourth rail 148, and a fourth slider 144b inside the vertical fourth rail 148. The lower thigh stand 14b is pivotally connected to the knee joint 15, and has a hole 144a, two vertical fourth rails 148, and two fourth sliders 144b inside the vertical fourth rails 148.

Three fourth bolts 144 pass through the three holes 144a and the three fourth sliders 144b inside the two vertical fourth rails 148. Therefore, the upper thigh stand 14a and the lower thigh stand 14b are connected through three fourth sliders 144b in the two vertical fourth rails 148, and can be moved from each other along the two vertical fourth rails 148 by loosening but not detaching the fourth bolts 144 from the fourth sliders 144b to extend or contract the thigh stand 14 so that the length of the thigh stand 14 is adjustable to fit the thigh length of the user.

The vertical fourth rail 148 of the upper thigh stand 14a and the vertical fourth rail 148 of the lower thigh stand 14b include expanded sections 148a to put the fourth sliders 144b inside the vertical fourth rails 148 of the upper thigh stand 14a. The vertical fourth rail 148 of the lower thigh stand 14b includes an open end 148b to put the fourth slider 144b inside the vertical fourth rail 148 of the lower thigh stand 14b.

Further, a fifth slider 612 can be put into a vertical fifth rail 149 of the lower thigh stand 14b through the open end 149a of the vertical fifth rail 149. A shield 61 can engage the fifth rail 149 through the fifth slider 612. Fifth bolts 614 pass through the shield 61 and are screwed into the fifth slider 612 inside the vertical fifth rails 149. Therefore, the shield 61 and the lower thigh stand 14b are connected through the fifth slider 612 in the vertical fifth rail 149. By loosening but not detaching the fifth bolts 614 from the fifth slider 612, the shield 61 can be moved along the vertical fifth rail 149 of the lower thigh stand 14b so that the position of the shield 61 is adjustable to fit the need of the user.

Moreover, a seventh slider 622 can be put into the vertical fifth rail 149 of the lower thigh stand 14b through the open end 149a of the vertical fifth rail 149, too. A thigh support 62 can engage the fifth rail 149 through the seventh slider 622. Seventh bolts 624 pass through horizontal second slots 62a of the thigh support 62 and are screwed into the seventh slider 622 inside the vertical fifth rails 149. Therefore, the thigh support 62 and the lower thigh stand 14b are connected through the seventh slider 622 in the vertical fifth rail 149. By loosening but not detaching the seventh bolts 624 from the seventh slider 622, the thigh support 62 can be moved along the vertical fifth rail 149 or the horizontal second slots 62a so that the position of the thigh support 62 is adjustable vertically and horizontally to fit the need of the user.

Figure 9C:
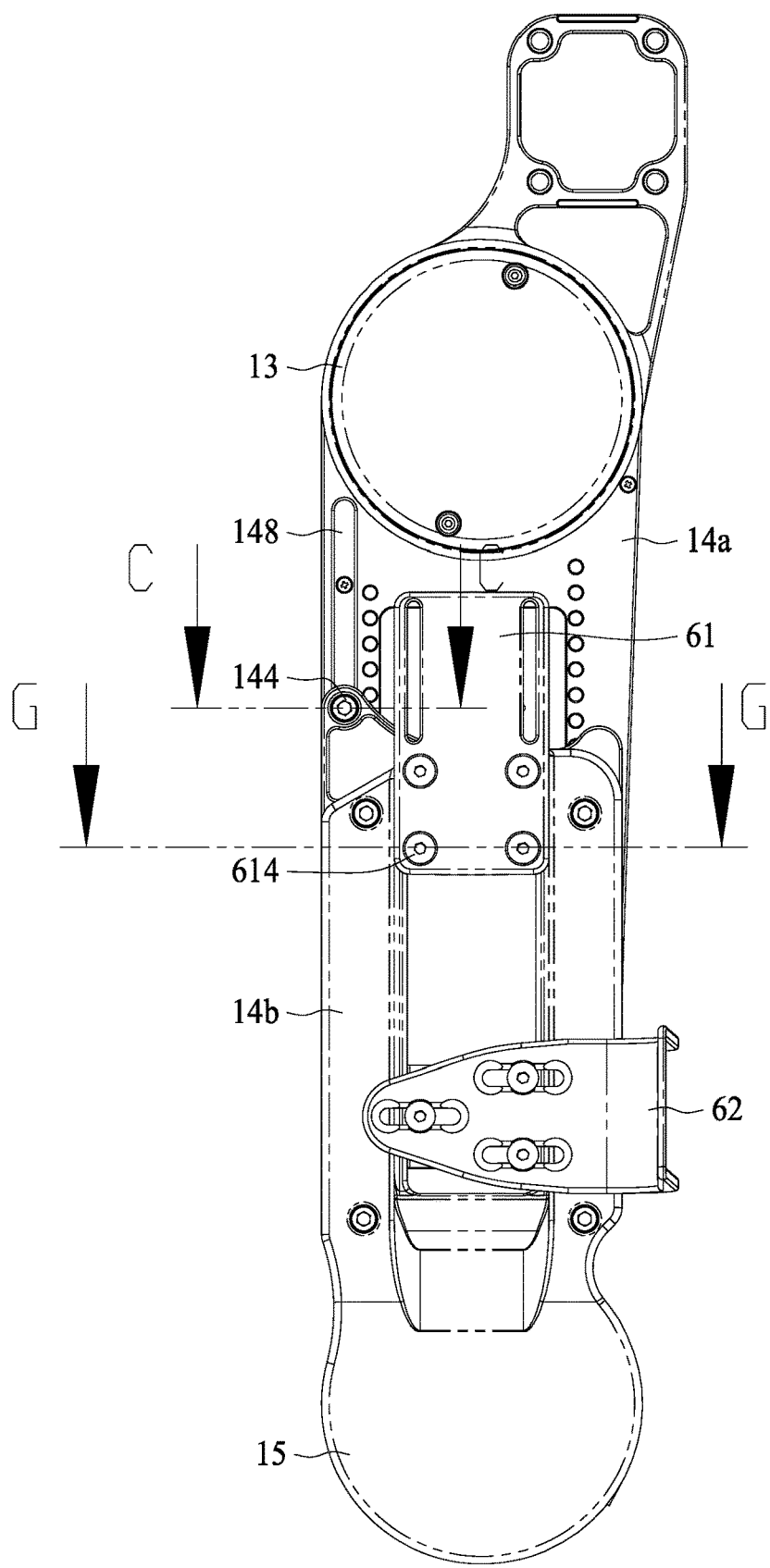
FIG. 9C is a left side view of the thigh stand in accordance with some embodiments of the present disclosure.

FIG. 9C is a left side view of the thigh stand 14 in accordance with some embodiments of the present disclosure.

Figure 10A:
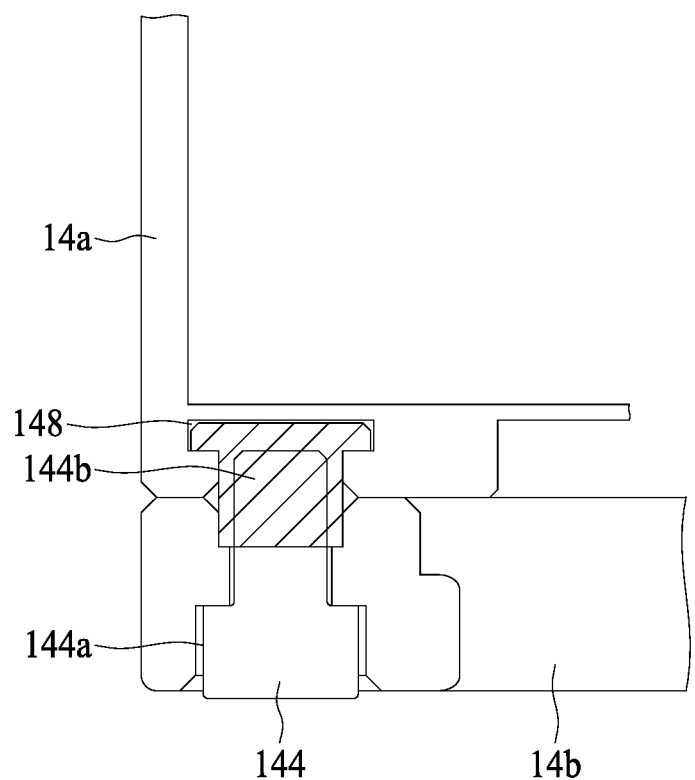
FIGS. 10A and 10B are cross-sectional views along Lines C-C, and G-G of FIG. 9C.

FIG. 10A is a cross-sectional view along Line C-C of FIG. 9C. Referring to FIG. 10A, the fourth bolt 144 passes through the hole 144a of the lower thigh stand 14b, and is screwed into the fourth slider 144b inside the fourth rail 148. The cross-section of the fourth rail 148 is a groove with two steps in two sides to contain the fourth slider 144b and prevent the fourth slider 144b from being pulled out of the fourth rail 148.

Figure 10B:
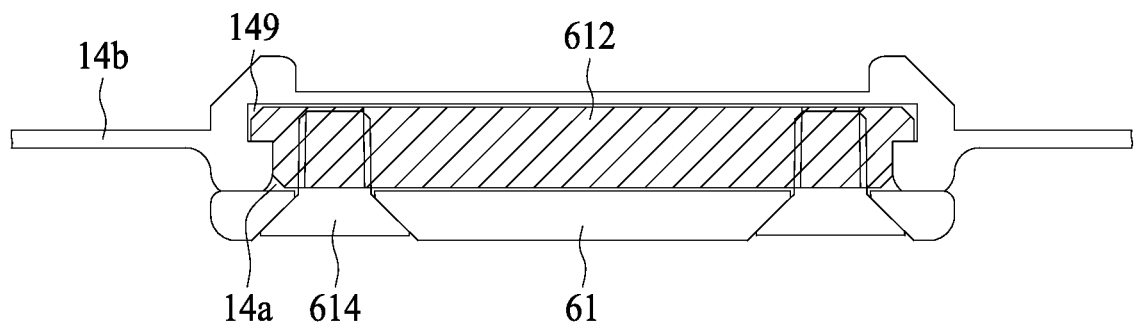

FIG. 10B is a cross-sectional view along Line G-G of FIG. 9C. Referring to FIG. 10B, the fifth bolt 614 passes through the shield 61, and is screwed into the fifth slider 612 inside the fifth rail 149. The cross-section of the fifth rail 149 is a groove with two steps in two sides to contain the fifth slider 612 and prevent the fifth slider 612 from being pulled out of the fifth rail 149.

Figure 11A:
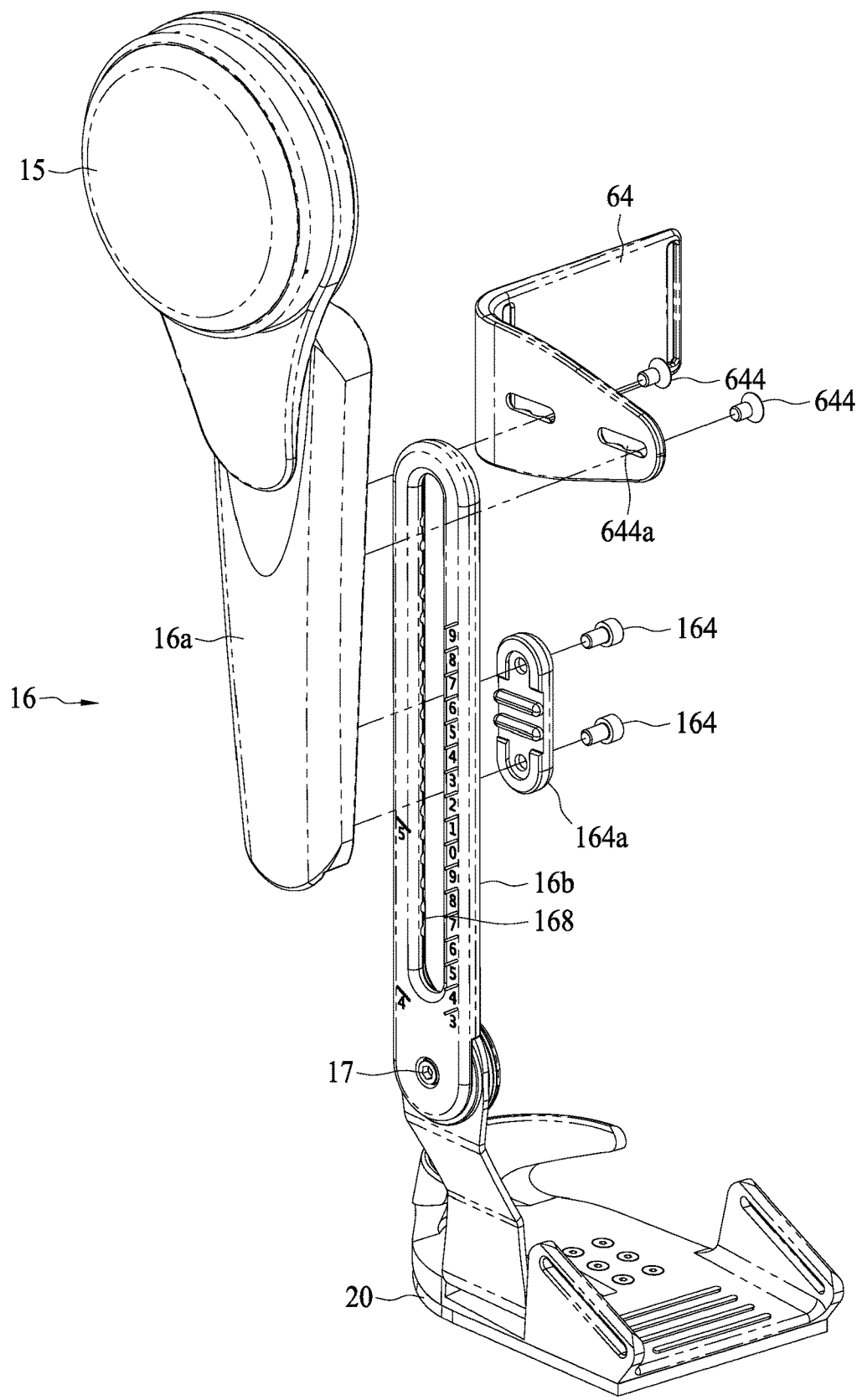
FIG. 11A is an exploded view of the shank stand viewed from the right side in accordance with some embodiments of the present disclosure.
Figure 11B:
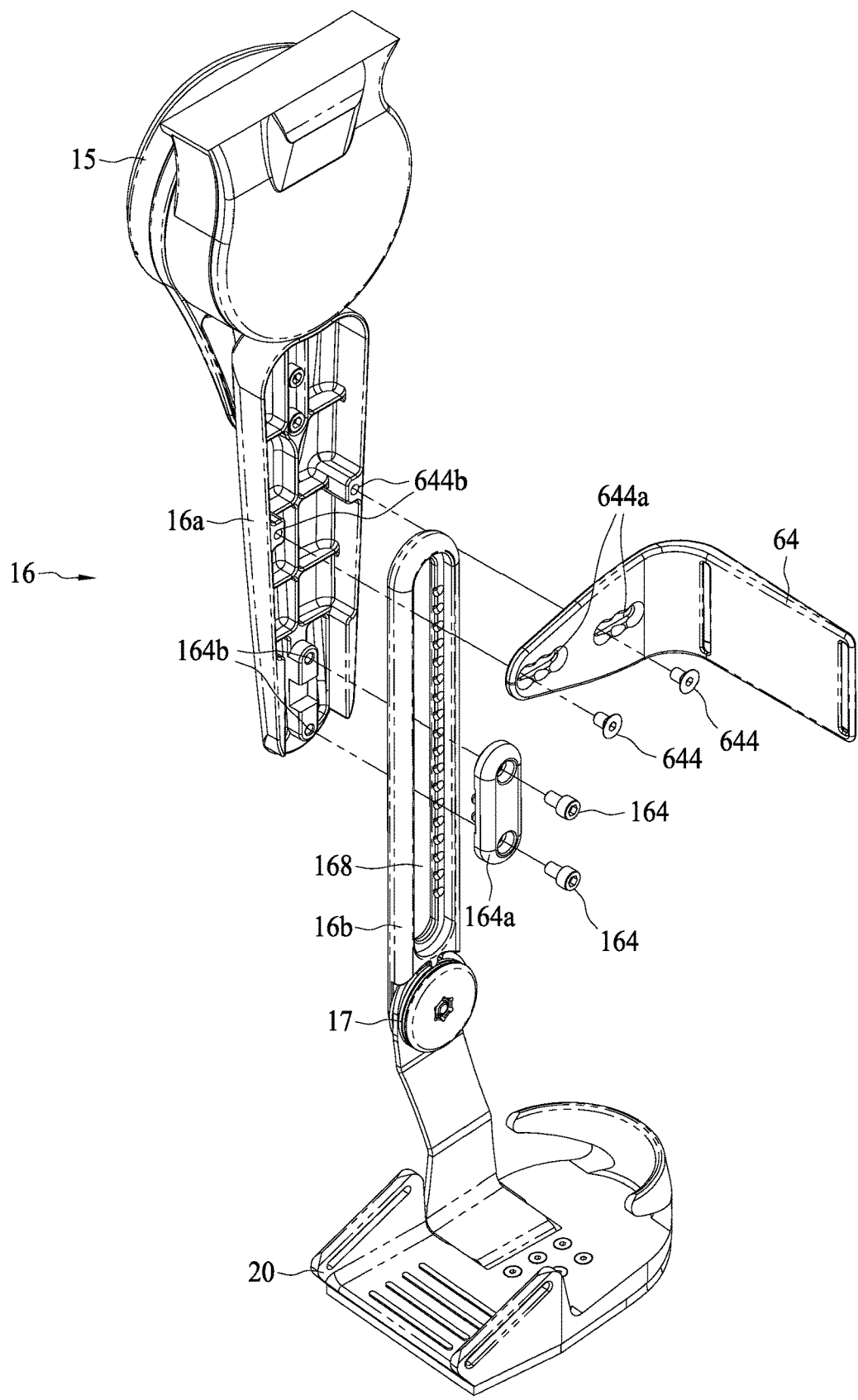
FIG. 11B is an exploded view of the shank stand viewed from the left side in accordance with some embodiments of the present disclosure.

FIG. 11A is an exploded view of the shank stand 16 viewed from the right side in accordance with some embodiments of the present disclosure. FIG. 11B is an exploded view of the shank stand 16 viewed from the left side in accordance with some embodiments of the present disclosure. Referring to FIGS. 11A and 11B, the shank stand 16 includes an upper shank stand 16a and a lower shank stand 16b. The upper shank stand 16a includes a center space to contain the lower shank stand 16b.

The upper shank stand 16a is pivotally connected to the knee joint 15, and has two holes 164b. The lower shank stand 16b is pivotally connected to the ankle joint 17, and has a vertical sixth rail 168, and a sixth slider 164a inside the vertical sixth rail 168.

Two sixth bolts 164 pass through the sixth slider 164a inside the vertical sixth rail 168 and are screwed into the holes 164b. Therefore, the upper shank stand 16a and the lower shank stand 16b are connected through the sixth slider 164a in the vertical sixth rails 168. By loosening but not detaching the sixth bolts 164 from the sixth slider 164a, the upper shank stand 16a and the lower shank stand 16b can be moved from each other along the vertical sixth rails 168 to extend or contract the shank stand 16 so that the length of the shank stand 16 is adjustable to fit the shank length of the user.

Moreover, a shank support 64 can engage the upper shank stand 16a. The bolts 644 pass through horizontal slots 644a of the shank support 64 and are screwed into holes 644b of the upper shank stand 16a. Therefore, the shank support 64 is fixed in the upper shank stand 16a, and the shank support 64 can be moved with the upper shank stand 16a along the vertical sixth rail 168 of the lower shank stand 16b so that the position of the shank support 64 is adjustable to fit the need of the user. By loosening but not detaching the bolts 644 from the holes 644b of the upper shank stand 16a, the shank support 64 can be adjusted forward and backward along the horizontal slots 644a.

Figure 11C:
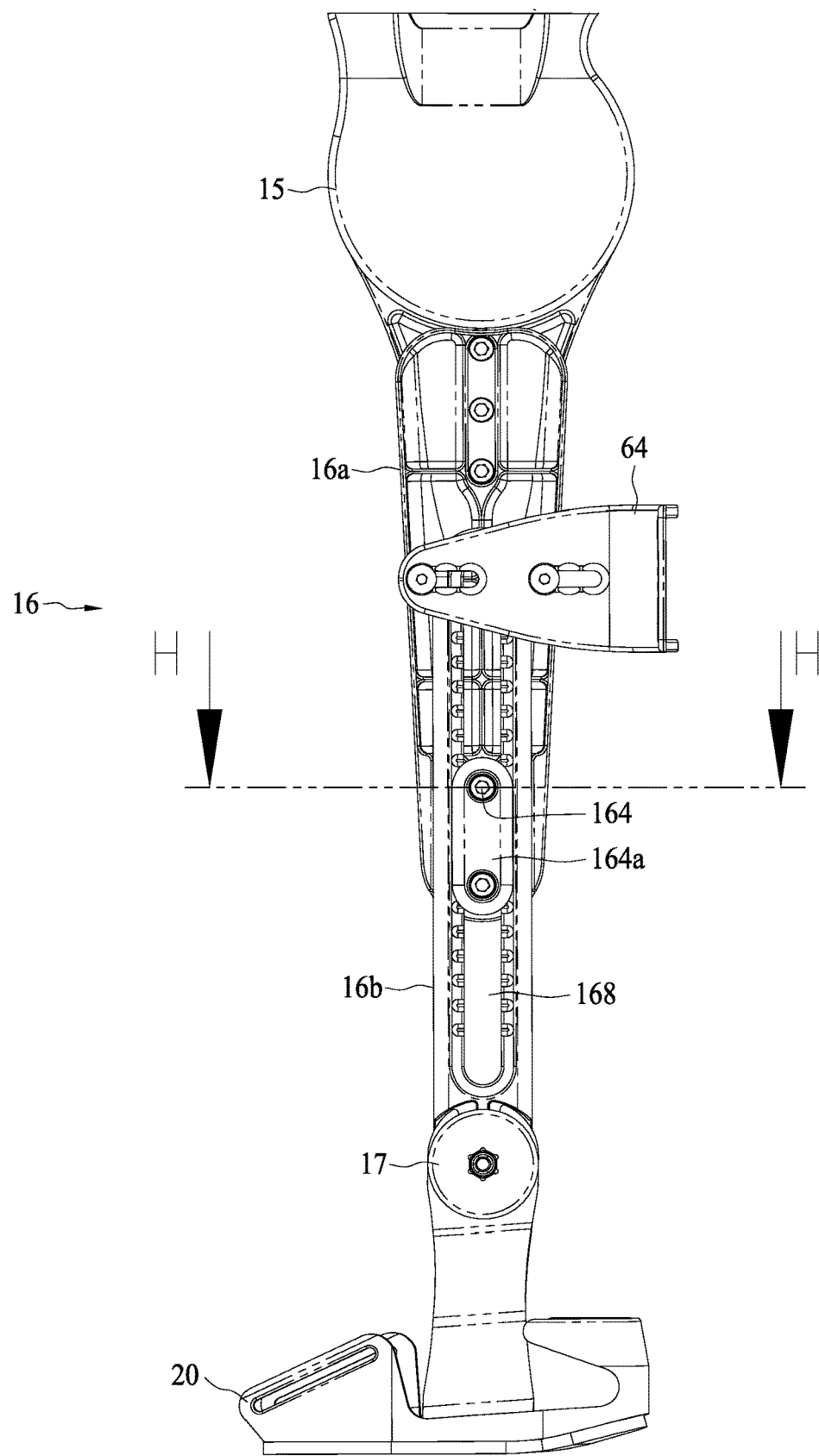
FIG. 11C is a left side view of the shank stand in accordance with some embodiments of the present disclosure.
Figure 12:
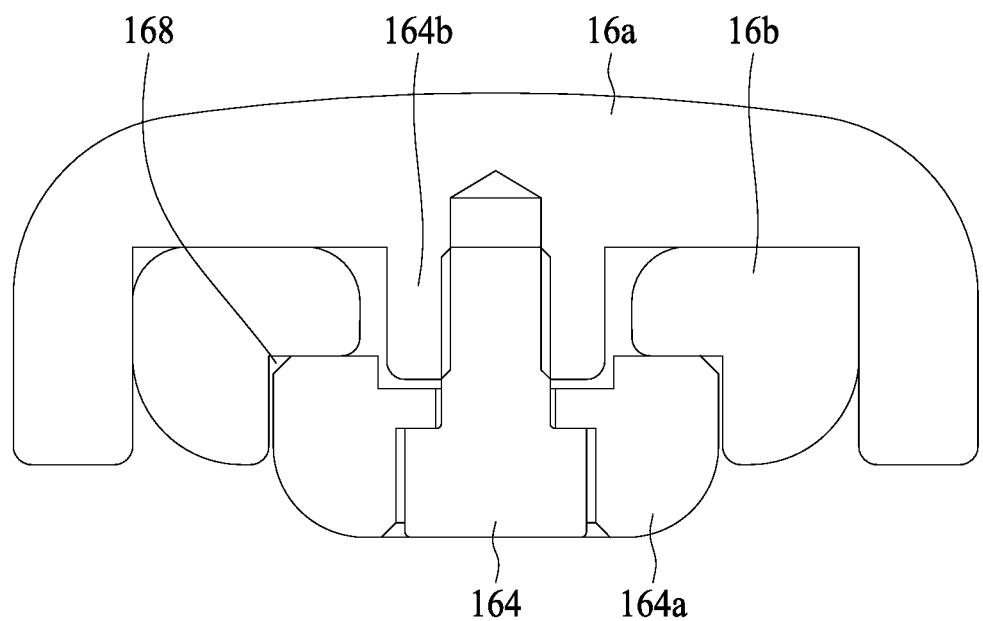
FIG. 12 is a cross-sectional view along Line H-H of FIG. 11C.

FIG. 11C is a left side view of the shank stand 16 in accordance with some embodiments of the present disclosure. FIG. 12 is a cross-sectional view along Line H-H of FIG. 11C. Referring to FIGS. 11C and 12, the sixth bolt 164 passes through the sixth slider 164a inside the sixth rail 168, and is screwed into the hole 164b. The cross-section of the sixth rail 168 is a groove with two steps in two sides to contain the sixth slider 164a and prevent the sixth slider 164a from being pulled out of the sixth rail 168.

Based on some embodiments of the disclosure, by using the slots and the rails to connect two elements, such as frames, assemblies or stands, of the exoskeleton robot, a relative position of the two elements is adjustable by sliding the slider, the screws or the bolts without fully disengaging the screws or the bolts from the elements. Thus, there are advantages to save effort to adjust the relative position of the elements of the exoskeleton robot to fully meet adjustment requirements, including a chest width, a hip depth, a thigh length, a thigh circumference, a shank length, and a shank circumference.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An exoskeleton robot, comprising:
    a waist assembly including:
        a first frame including a first rail and a first slider inside the first rail,
        a plate fixed by a first bolt screwed into the first slider, and
        a second frame connected to the plate, wherein the second frame having a first slot and a second bolt inside the first slot;
    a leg assembly installed to the second frame by the second bolt;
    a back stand installed to the first frame; and
    a chest assembly installed to the back stand and including:
        a third frame installed to the back stand and having a second rail and a second slider inside the second rail; and
        a chest board installed to the third frame and fixed by a third bolt screwed into the second slider.

2. The exoskeleton robot of claim 1, wherein the second frame is connected to the plate through a joint, and the second frame is pivotally connected to the plate.

3. The exoskeleton robot of claim 1, wherein the first rail includes an expanded section to allow the first slider put into the first rail through the expanded section.

4. The exoskeleton robot of claim 3, wherein the back stand includes a rail cover installed on the expanded section and covering the expanded section.

5. The exoskeleton robot of claim 1, wherein the back stand includes a third rail and a third slider inside the third rail.

6. The exoskeleton robot of claim 1, wherein the leg assembly comprises a thigh stand, a knee joint, and a shank stand connected to the thigh stand with the knee joint.

7. The exoskeleton robot of claim 1, wherein the first rail is horizontal and allows the first slider to move horizontally.

8. The exoskeleton robot of claim 1, wherein the first slot is horizontal and allows the second bolt to move horizontally.

9. The exoskeleton robot of claim 1, wherein the first frame includes another first slider inside the first rail.

10. The exoskeleton robot of claim 1, wherein the first slot includes multiple indentations along the first slot to fit a head of the second bolt.

11. The exoskeleton robot of claim 1, wherein the third frame includes two wings, each of the two wings has the second rail and the second slider inside the second rail.

12. The exoskeleton robot of claim 5, wherein the third rail is vertical and allows the third slider moving vertically.

13. The exoskeleton robot of claim 1, wherein the second rail is horizontal and allows the second slider to move horizontally.

14. The exoskeleton robot of claim 1, wherein the leg assembly includes:
    a hip joint; and
    a thigh stand including:
        an upper thigh stand connected to the hip joint, including a first hole, a fourth rail and a fourth slider inside the fourth rail, wherein the fourth rail is vertical and allows the fourth slider to move vertically,
        a lower thigh stand including a fifth rail and a fifth slider inside the fifth rail wherein the fifth rail is vertical and allows the fifth slider to move vertically; and a fourth bolt passing through the first hole and screwed into the fourth slider.

15. The exoskeleton robot of claim 14, further comprising:
a knee joint connected to the lower thigh stand; and
a shank stand including:
a lower shank stand including a sixth rail and a sixth slider inside the sixth rail, wherein the sixth rail is vertical and allows the sixth slider to move vertically, and
an upper shank stand connected to the knee joint and fixed by a sixth bolt screwed into the sixth rail.

16. The exoskeleton robot of claim 14, wherein the lower thigh stand includes:
a thigh support with a second slot and a seventh bolt; and
a seventh slider inside the fifth rail, wherein the fifth rail is vertical and allows the seventh slider to move along the fifth rail vertically,
wherein the seventh bolt passes through the thigh support and screwed into the seventh slider.

17. The exoskeleton robot of claim 16, wherein the second slot is horizontal and allows the seventh bolt to move along the second slot horizontally.

18. The exoskeleton robot of claim 14, wherein the lower thigh stand includes a shield, the fifth bolt passes through the shield and screwed into the fifth slider.

19. The exoskeleton robot of claim 15, wherein the shank stand includes a shank support installed in the upper shank stand.

20. The exoskeleton robot of claim 15, wherein the upper shank stand includes a center space to contain the lower shank stand.

* * * * *